(12) United States Patent
Kita et al.

(10) Patent No.: US 8,703,157 B2
(45) Date of Patent: Apr. 22, 2014

(54) PHASE TRANSITIONING HYDROGELS

(75) Inventors: Kristin B. Kita, Conshohocken, PA (US); Nigel G. Smith, Norwich (GB); Anthony M. Lowman, Wallingford, PA (US); Garland W. Fussell, Thorndale, PA (US); Michael F. Keane, Downingtown, PA (US)

(73) Assignees: DePuy Synthes Products, LLC, Raynham, MA (US); Drexel University, Philadelphia, PA (US)

( * ) Notice: Subject to any disclaimer, the term of this patent is extended or adjusted under 35 U.S.C. 154(b) by 186 days.

(21) Appl. No.: 12/994,336

(22) PCT Filed: May 27, 2009

(86) PCT No.: PCT/US2009/045328
§ 371 (c)(1),
(2), (4) Date: Feb. 16, 2011

(87) PCT Pub. No.: WO2009/146331
PCT Pub. Date: Dec. 3, 2009

(65) Prior Publication Data
US 2011/0270400 A1    Nov. 3, 2011

Related U.S. Application Data

(60) Provisional application No. 61/056,197, filed on May 27, 2008.

(51) Int. Cl.
*A61K 9/00* (2006.01)

(52) U.S. Cl.
USPC ............... 424/400; 424/422; 424/423; 516/9; 516/17

(58) Field of Classification Search
None
See application file for complete search history.

(56) References Cited

U.S. PATENT DOCUMENTS

| 2004/0171740 A1* | 9/2004 | Ruberti et al. ................ 524/563 |
| 2005/0191270 A1* | 9/2005 | Gruening et al. ............ 424/78.3 |

FOREIGN PATENT DOCUMENTS

WO    WO2005/080477    9/2005

OTHER PUBLICATIONS

Inamura I, Liquid-Liquid Phase Separation and Gelation in the Poly-(vinyl alcohol)-Poly(ethylene glycol)-Water System . . . , Polymer Journal, Society of Polymer Scienct, Tokyo, JP, vol. 18, No. 3, Jan. 1, 1986; pp. 269-272.

Int'l Search Report dated Aug. 4, 2009 for corresponding appln. No. PCT/US09/045328.

Pereira, et al., Liquid-Liquid Equilibrium Phase Diagrams of New Aqueous Two-Phase Systems . . . , J. Chem. Eng. Data, vol. 49, No. 1, 2004, pp. 43-47.

\* cited by examiner

*Primary Examiner* — James Rogers
(74) *Attorney, Agent, or Firm* — Stradley Ronon Stevens & Young, LLP

(57) ABSTRACT

A method of forming and the resulting hydrogel composition comprising poly(vinyl alcohol) at a final concentration of about 20% (w/w) to about 65% (w/w) and polyethylene glycol at a final concentration of about 2% (w/w) to about 20% (w/w), wherein the hydrogel composition has a total polymer content, above about 30% (w/w), higher than the total polymer content of a precursor polymer solution formulated prior to the formulation of the hydrogel composition. The hydrogel composition may further comprise poly(vinyl pyrrolidone) at a final concentration of about 0.10% (w/w) to about 0.75% (w/w).

23 Claims, 23 Drawing Sheets ent content, above about 30% (w/w), higher than the
total polymer content of a precursor polymer solution formulated prior to the formulation of the hydrogel composition.
The hydrogel composition may further comprise poly(vinyl pyrrolidone) at a final concentration of about 0.10% (w/w) to about 0.75% (w/w).

PHASE TRANSITIONING HYDROGELS

CROSS-REFERENCE TO RELATED APPLICATIONS

This application is the National Stage of International Application No. PCT/US2009/045328, filed May 27, 2009, which claims the benefit of U.S. Provisional Application No. 61/056,197, filed May 27, 2008, the disclosures of which are incorporated herein by reference in their entireties for all purposes.

FIELD OF THE INVENTION

The present invention relates to a hydrogel composition comprising a biocompatible agent, such as, for example, polyethylene glycol (PEG) and polymer components such as, for example, poly(vinyl alcohol) (PVA), and/or poly(vinyl pyrrolidone) (PVP). The hydrogel composition having potential use as a replacement material for a spinal disc or for use in other body applications such as for use as a bearing surface in joint replacements, as void filling composition or other implant for cosmetic purposes.

BACKGROUND OF THE INVENTION

The human intervertebral disc is comprised of two major structures, an outer or peripheral tendinous structure often referred to as the disc annulus, and an inner gelatinous nucleus pulposus located in a generally central region. Degeneration of the nucleus pulposus, typically associated with natural aging, may lead to disc degradation and loss of function.

Chronic back pain caused by injury or age-related degeneration of an intervertebral disc is a condition experienced by many patients. Current treatments range from bed rest to invasive surgical procedures, including discectomy, spinal fusion and partial or total disc replacement.

A partial or full discectomy may relieve back pain to a patient caused by nerve impingement but it will not restore healthy physiologic function to the disc or prevent additional wear or deterioration of the disc or its annulus. Replacement or supplementation of the nucleus pulposus can relieve pain, restore healthy physiologic function to the disc and/or prevent additional wear or deterioration of the annulus. Currently, few minimally invasive techniques exist for supplementation or replacement of the nucleus pulposus of a spinal disc into a selected site of a mammal. Even fewer techniques can provide the physiological/mechanical properties to restore the damaged disc to its full capacity.

Accordingly, it is desirable to provide an implant, system and technique for repairing a damaged intervertebral disc. Other objects and advantages of the present invention shall become apparent from the accompanying description and examples.

BRIEF SUMMARY OF THE INVENTION

The present invention relates to hydrogel composition comprising a biocompatible agent, such as, for example, polyethylene glycol (PEG) and polymer components such as, for example, poly(vinyl alcohol) (PVA), and/or poly(vinyl pyrrolidone) (PVP).

One preferred embodiment may comprise a hydrogel composition comprising poly(vinyl alcohol) at a final concentration of about 20% (w/w) to about 65% (w/w) and polyethylene glycol at a final concentration of about 2% (w/w) to about 20% (w/w), wherein the hydrogel composition has a total polymer content, above about 30% (w/w), higher than the total polymer content of a precursor polymer solution formulated prior to the formulation of the hydrogel composition. The hydrogel composition may further comprise poly(vinyl pyrrolidone) at a final concentration of about 0.10% (w/w) to about 0.75% (w/w).

Another preferred embodiment may comprise a resultant hydrogel composition comprising poly(vinyl alcohol) and polyethylene glycol, the hydrogel composition formulated by first preparing a solution of poly(vinyl alcohol), then adding the polyethylene glycol to form a precursor polymer solution, such that a phase separation occurs resulting in the formation of a liquid aqueous supernatant and the resultant hydrogel composition which has a total polymer content higher than the total polymer content of the precursor polymer solution. The resultant hydrogel composition may further comprise poly(vinyl pyrrolidone). The hydrogel composition also may be formulated by cooling the precursor polymer solution after the polyethylene glycol has been added and allowing the phase separation to occur resulting in the formation of the liquid aqueous supernatant and the resultant hydrogel composition. The resultant hydrogel composition may have poly(vinyl pyrrolidone) at a final concentration of about 0.10% (w/w) to about 0.75% (w/w). The resultant hydrogel composition may have poly(vinyl alcohol) at a final concentration of about 20% (w/w) to about 65% (w/w). The resultant hydrogel composition may have polyethylene glycol at a final concentration of about 2% (w/w) to about 20% (w/w).

The hydrogel composition may preferably have an osmotic pressure of at least 0.1 MPa. The hydrogel composition may preferably have a compressive chord modulus of about 50 kPa to about 5,000 kPa. The hydrogel composition may preferably have a viscosity at about 45° C. of about 0.02 kP to about 2.0 kP. The hydrogel composition may preferably have a viscosity at about 37° C. of at least 0.475 kP. The hydrogel composition may preferably further comprise a radiopaque component which may preferably be Barium Sulfate.

Another embodiment may comprise a method of implanting a resultant hydrogel composition into an interior cavity of an intervertebral disc of a spinal column of a patient comprising: providing a resultant hydrogel composition comprising poly(vinyl alcohol) at a final concentration of about 20% (w/w) to about 65% (w/w) and polyethylene glycol at a final concentration of about 2% (w/w) to about 20% (w/w); creating a passageway into the interior cavity of the intervertebral disc; heating the resultant hydrogel composition to about 65° C. to about 100° C. to provide an injectable composition; injecting the hydrogel composition into the interior cavity of the intervertebral disc of the spinal column; and permitting the hydrogel composition to solidify to form a solid implant. The hydrogel compositions may further comprise poly(vinyl pyrrolidone) at a final concentration of about 0.10% (w/w) to about 0.75% (w/w).

A further embodiment may comprise a method of formulating a resultant hydrogel composition comprising poly(vinyl alcohol) and polyethylene glycol comprising: preparing a solution of poly(vinyl alcohol); adding the polyethylene glycol to form a precursor polymer solution; allowing the polyethylene glycol to remove water from the precursor polymer solution thereby resulting in the formation of a liquid aqueous supernatant and the resultant hydrogel composition, the resultant hydrogel composition having a total polymer content higher than the total polymer content of the precursor polymer solution. The resultant hydrogel composition may further comprise poly(vinyl pyrrolidone). The resultant hydrogel composition may have poly(vinyl pyrrolidone) at a final concentration of about 0.10% (w/w) to about 0.75% (w/w). The resultant hydrogel composition may have poly(vinyl alcohol) at a final concentration of about 20% (w/w) to about 65% (w/w). The resultant hydrogel composition may have polyethylene glycol at a final concentration of about 2% (w/w) to about 20% (w/w).

BRIEF DESCRIPTION OF THE DRAWINGS

The foregoing summary, as well as the following detailed description of preferred embodiments of the application, will be better understood when read in conjunction with the appended drawings. The drawings, examples and embodiments described within this specification are to be understood as illustrative and exemplary of structures, features, compositions, techniques and aspects of the present invention and not as limiting the scope of the invention. It should be understood that the application is not limited to the precise arrangements, structures, features, uses, compositions, techniques and instrumentalities shown and that features and structures may be used singularly or in combination with other features and structures described in other or alternative embodiments. In the drawings.

DETAILED DESCRIPTION OF THE INVENTION

Figure 1:
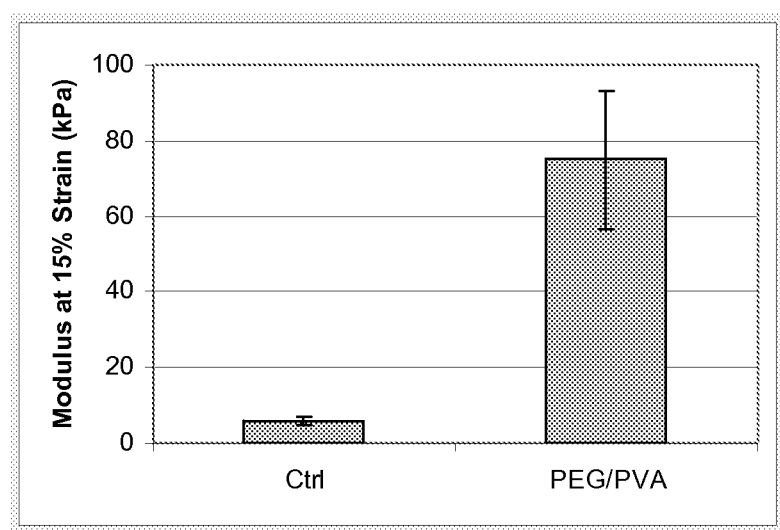
FIG. 1 is a graphical representation of compressive modulus of a resultant PVA/PEG hydrogel composition (15% PEG/PVA) molded for 30 minutes and a control PVA hydrogel composition (without PEG) molded for 4 hours.

The methods, examples and embodiments described within this specification are to be understood as illustrative and exemplary of the composition, structures, features, techniques and aspects of the present invention and not as limiting the scope of the invention. Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior", "lateral", "medial" and related words and/or phrases designate preferred positions and orientations in the human body to which reference is made and are not meant to be limiting. All percentages, unless otherwise indicated, are on a weight by weight (w/w) basis. The terminology includes the above-listed words, derivatives thereof and words of similar import.

While the hydrogel composition is described with respect to its use in spinal applications and for use as a replacement for the spinal disc nucleus, it should be recognized that it may have many other uses such as a cosmetic implant, or in other joints and locations in the body and in the spine. The hydrogel composition of the present invention may be formulated by adding a biocompatible agent, such as, for example, polyethylene glycol (PEG), to a polymer solution, for example, preferably a solution of poly(vinyl alcohol) (PVA), or a solution of PVA and poly(vinyl pyrrolidone) (PVP), resulting in a final hydrogel composition containing a higher polymer content than the original polymer solution. The biocompatible agent preferably draws water out of the polymer solution and may also act as a plasticizer in the final hydrogel composition by decreasing injection viscosity preferably at approximately 45° C. to about 95° C.

One exemplary manner of forming the hydrogel composition is as follows. First, an aqueous polymer solution may be prepared by dissolving the polymer or polymers in water at a temperature between about 87° C. and about 100° C., preferably about 95° C. Optionally, an autoclave may be employed at temperatures above 100° C. The polymer may be, for example, PVA alone, or PVA and PVP together. Second, a biocompatible agent, such as, for example, PEG may be added to the polymer solution at a temperature between about 65° C. and about 100° C., preferably about 75° C. creating a precursor polymer solution. A phase separation occurred resulting in the formation of a solid hydrogel and liquid supernatant phase. The hydrogel composition also may be formulated by cooling the precursor polymer solution after the polyethylene glycol has been added and allowing the phase separation to occur resulting in the formation of the liquid aqueous supernatant and the resultant hydrogel composition. The supernatant phase, which may consist of PEG in an aqueous solution, may be removed and discarded. The resulting solid hydrogel may be a hydrogel composition with a higher polymer content than the precursor polymer solution. Due to an incompatibility between PVA and PEG, the phase separation discussed above may occur which may concentrate the polymers of the hydrogel and improve the mechanical properties, such as, for example, elasticity, viscosity and compression modulus, of the resultant hydrogel composition.

The ratio of PVA to PEG in the precursor polymer solution may be from about 1:10 to about 20:1, preferably from about 1:3 to about 13:1, more preferably about 1:1.

One exemplary embodiment of a hydrogel composition may comprise, for example, the polymers PVA and PEG. The polymer content in the resultant hydrogel composition may be about 45% to about 82%.

Another exemplary embodiment of a hydrogel composition may comprise PVA, PVP and PEG. PVA may be at a final concentration of about 20% to about 65%, preferably about 29% to about 35%, more preferably 33.5%. PVP may be at a final concentration of about 0.10% to about 0.75%, preferably 0.25% to about 0.38%, more preferably about 0.3%. PEG may be at a final concentration of about 2% to about 20%, preferably about 6% to about 8%, more preferably about 6.5%.

The resultant hydrogel may have a compressive chord modulus of about 50 kPa to about 5,000 kPa, preferably about 100 kPa to about 2,500 kPa, more preferably about 450 kPa.

The resultant hydrogel may have a pre-set viscosity at 45° C. of about 0.02 kP to about 2.0 kP, preferably about 0.2 kP to about 1.0 kP, more preferably about 0.8 kP.

The resultant hydrogel may have a post-set viscosity at 37° C. of about 0.475 kP, preferably at least 0.475 kP.

The hydrogel composition may be made to be radiopaque for visualization during and after implantation by the addition of a radiopaque component, such as Barium Sulfate, iodine containing materials, and other known radiopacifiers. This radiopaque component may be added to the composition during the initial polymer solution making process or anytime up to and including mixing the components, immediately prior to injection or during implantation of the hydrogel.

Once the water-rich supernatant phase is removed from the resultant hydrogel composition, the resultant hydrogel may be molded, while heated to approximately 75° C., into a package for solidification. The package may serve as a cartridge for the delivery of the resultant hydrogel to the patient. The cartridge containing the solidified resultant hydrogel may then be double packed and subjected to heat sterilization. The resultant hydrogel may also be dried into a solid preformed implant device that can be rehydrated prior to use as an injectable implant.

After final packaging of the sterilized hydrogel product, the resultant hydrogel composition may be delivered to the operating room where the inner pouch of the double package may be opened and the cartridge inserted into a delivery device such as, for example, a delivery gun with a temperature controller.

Inside the gun, the resultant hydrogel composition, which may not be injectable at room temperature (i.e., between about 22° C. and about 27° C.), or operating room temperature (i.e., between about 17° C. and about 27° C.) may be heated to about 65° C. to about 100° C. for a sufficient amount of time to increase thermal energy to mobilize intermolecular and intramolecular associations between the polymers and maintain flowability of the composition. After a sufficient length of heating time, the now flowable resultant hydrogel composition may then be delivered by a means such as, for example, injection from the gun down a cannula and into a target site, such as a cavity created in the intervertebral nucleus pulposus. The flowable resultant hydrogel composition preferably is injected at less than about 95° C. to minimize and prevent any damage or necrosis to body tissues, cells and organs as a result of excessive heat from the hydrogel. The resultant hydrogel composition may cool in the target site and preferably become an elastic solid upon cooling to approximately 45° C. in the target site.

In contrast to known implant compositions that are based upon reactive, elastomer forming systems such as silicones or polyurethanes, the resultant hydrogel composition of the present invention contains no catalysts or leachable molecules thus preventing damage to nearby tissue in proximity to the hydrogel.

The resultant hydrogel composition of the present invention may be used as a soft tissue replacement or repair, as a non-rigid implant biomaterial, etc. While the hydrogel may generally be used in the spine (for example, in the lumbar, thoracic or cervical regions) as a nucleus replacement, those skilled in the art will appreciate that the hydrogel may be used in other parts of the body. The hydrogel may also have other applications and uses, such as, for example, in other joints and as a cosmetic implant, and should not be limited to the structure or use described and illustrated.

EXAMPLES AND EXPERIMENTS

The following examples and experiments describe some of the properties of the preferred resultant hydrogel composition described herein and are only intended to assist in explaining and illustrating the arrangements, composition, structures, properties, features, techniques and aspects of the resultant hydrogel composition and its intermediaries and not as limiting the scope of the invention to the precise arrangements, compositions, structures, properties, features techniques, methods of manufacturing and aspects described.

Example 1

Preparation of and Mechanical Testing of PVA/PEG Hydrogel Compositions

To demonstrate the properties of a resultant PVA/PEG hydrogel composition, PVA/PEG hydrogel composition samples were subjected to mechanical testing.

PVA/PEG hydrogel composition samples were formulated by first preparing an aqueous PVA solution (28% w/w) by mixing PVA ((Mowiol 28-99: 145 kDa; fully hydrolyzed) supplied by Kuraray Specialties Europe) and deionized water in sealed glass bottles and heating at 121° C. for 30 minutes in an autoclave. Solutions were then stored at 75° C. in a water bath. The PVA solution was maintained at 75° C.±1° C. during the addition of PEG ((10 kDa Sigma Aldrich Cat.

81280) supplied by Fluka) to a final concentration of 15% w/w to create a precursor polymer solution. The initial concentration ranges of the components of the precursor polymer composition are summarized in Table 1. The precursor PVA/PEG solution was then cooled in a 37° C. water bath for two hours so that it was equilibrated at 37° C. During equilibration a solid resultant hydrogel and an aqueous supernatant were formed. The supernatant was then decanted from the resultant hydrogel. Then the resultant hydrogel was heated to 121° C. in an autoclave which returned the hydrogel to a flowable state. The resultant hydrogel composition was stored in a 75° C. water bath until use.

TABLE 1

Concentrations of Components of the Precursor PVA/PEG Solution

| Material | % w/w | mmol |
|---|---|---|
| Polyethylene glycol 10 kDa | 15.0 | 0.045 |
| Polyvinyl alcohol 145 kDa | 23.8 | 0.005 |
| Deionized water | 61.2 | 102 |

Cylindrical samples (n=4) (approximately 8 mm in height and 12 mm in diameter) were molded directly from the PVA/PEG resultant hydrogel composition at 75° C. by injecting the flowable PVA/PEG resultant hydrogel composition into a sealed cylindrical mold pre-equilibrated to 37° C. The mold was maintained at 37° C. for 30 minutes. Control PVA only (i.e., no PEG) hydrogel cylinders were made by solubilizing PVA in deionized water, injecting the solution into a mold and allowing the hydrogel to form at 37° C. for approximately 30 minutes.

The test cylinders were removed from the mold and tested in compression (at a rate of 100% strain/min) on an Instron (Model #3342). FIG. 1 demonstrates that there is a significant increase in compression modulus for cylinders made from the resultant PVA/PEG hydrogel composition when compared with control cylinders molded from the same grade of PVA alone (i.e., no PEG).

Example 2

Polymer Content of the PVA/PEG Hydrogel Compositions

Three resultant PVA/PEG hydrogel compositions were formed as described in Example 1. The water content was calculated for the three PVA/PEG hydrogel compositions to be 51.7% on average with a standard deviation of 0.65 (See Table 2); the remaining 48.3% is polymer.

TABLE 2

Concentration of Components of the Resultant PVA/PEG Hydrogel Composition

| Material | Composition (% w/w) |
|---|---|
| Water | 51.7 |
| Polymer (PEG/PVA) | 48.3 |

Example 3

Figure 2:
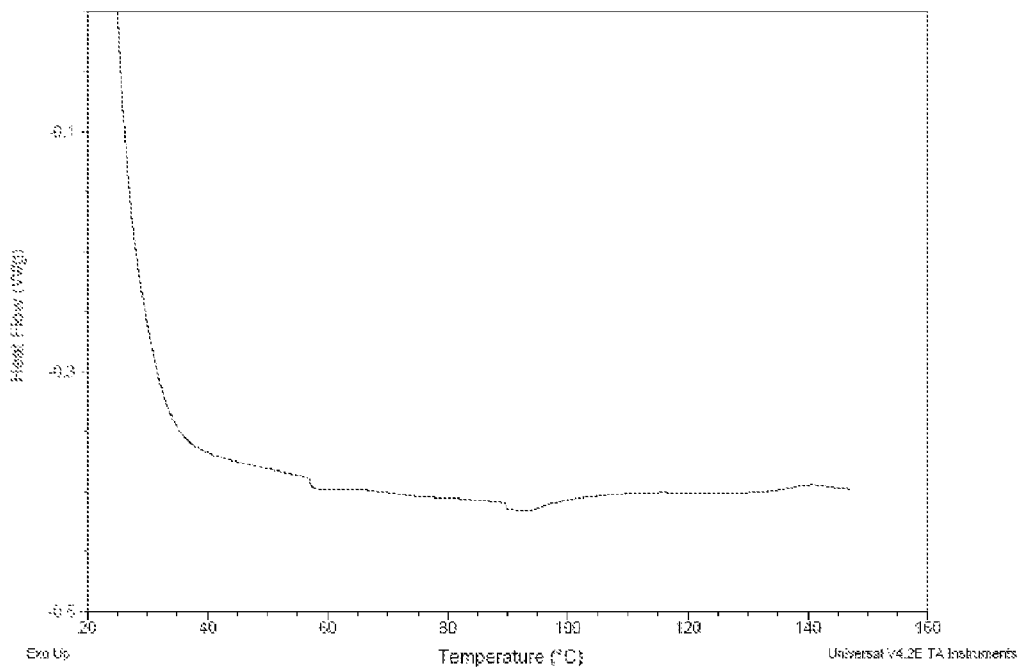
FIG. 2 is a graphical representation of the differential scanning calorimetry thermogram of a PVA/PEG hydrogel composition.

Differential Scanning Calorimetry Analysis of the Resultant PVA/PEG Hydrogel Compositions The thermal transitions for resultant PVA/PEG hydrogel compositions, as prepared in Example 1, were investigated using differential scanning calorimetry (DSC). calorimetry was performed at a ramp of 2° C./min from 25° C. to 150° C. FIG. 2 is a graph of heat flow in Watts/gram (W/g) versus temperature. Two major melt transitions were observed for the PVA/PEG hydrogel compositions. The first melt transition was observed when the resultant PVA/PEG hydrogel composition was heated to approximately 55° C. to 65° C. The second melt transition was observed as the resultant PVA/PEG hydrogel composition was heated to approximately 90° C. to 97° C. The melt transitions are depicted on the graph as slight dips in the curve at the indicated temperatures. The observed melt transitions may be due to the melting out of crystallites (e.g., undissolved PEG) and specific chain associations within the hydrogel. The composition without PEG did not exhibit these melt transitions.

Example 4

Compositional Analysis of the Resultant PVA/PEG Hydrogel Compositions

A series of precursor PVA/PEG solutions of varying ratios of PVA to PEG were prepared, as described in Example 1, to determine the mass and polymer content of the resultant hydrogels. The overall water content of the precursor polymer solutions was maintained at 60% w/w for all compositions. The PVA/PEG ratios were varied to determine the effect of PVA/PEG ratio on the resultant hydrogel composition. Table 3 describes the compositions investigated.

TABLE 3

Concentrations of Components in the Precursor Polymer Solutions

| PVA/PEG weight ratio | PVA Mass (g) | Wt % | mmol | PEG Mass (g) | Wt % | mmol | Water Mass (g) | Wt % | mmol |
|---|---|---|---|---|---|---|---|---|---|
| 25:15 | 2.94 | 25% | 0.020 | 1.76 | 15% | 0.176 | 7.06 | 60% | 392 |
| 22.5:17.5 | 2.73 | 22.5% | 0.019 | 2.12 | 17.5% | 0.212 | 7.27 | 60% | 404 |
| 20:20 | 2.50 | 20% | 0.017 | 2.50 | 20% | 0.250 | 7.50 | 60% | 417 |
| 10:30 | 1.43 | 10% | 0.010 | 4.29 | 30% | 0.429 | 8.57 | 60% | 476 |

Figure 3:
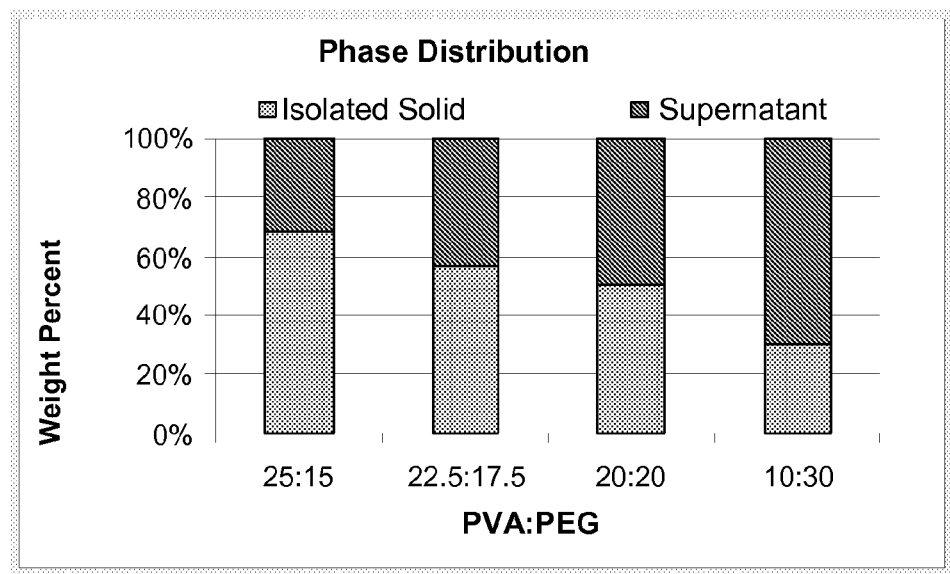
FIG. 3 is a graphical representation of the phase distribution of PVA/PEG hydrogel compositions at differing ratios of components.

Following incubation of the PVA/PEG solution in a 37° C. water bath for approximately two to three hours so that equilibration was reached, the PVA/PEG hydrogels separated into two phases. The mass of the isolated solid hydrogel was determined by separating it from the supernatant and weighing it. The mass of the supernatant phase was calculated by subtracting the mass of the solid hydrogel from the original mass of the composition. FIG. 3 shows the weight percent distribution of the two phases for each of the PVA/PEG ratios examined.

FIG. 3 indicates that the weight percent of the isolated resultant solid hydrogel ranged from approximately 30% of the total mass (i.e., mass of the hydrogel and the supernatant combined) for the 10:30 PVA:PEG ratio to approximately 68% of the total mass for the 25:15 PVA:PEG ratio. Therefore, the mass of the supernatant (liquid) phase ranged from approximately 32% to 70% of the total mass. This data indicates that the distribution of the two phases, solid hydrogel and liquid supernatant, may be dependant on the initial PVA/PEG ratio.

Figure 4:
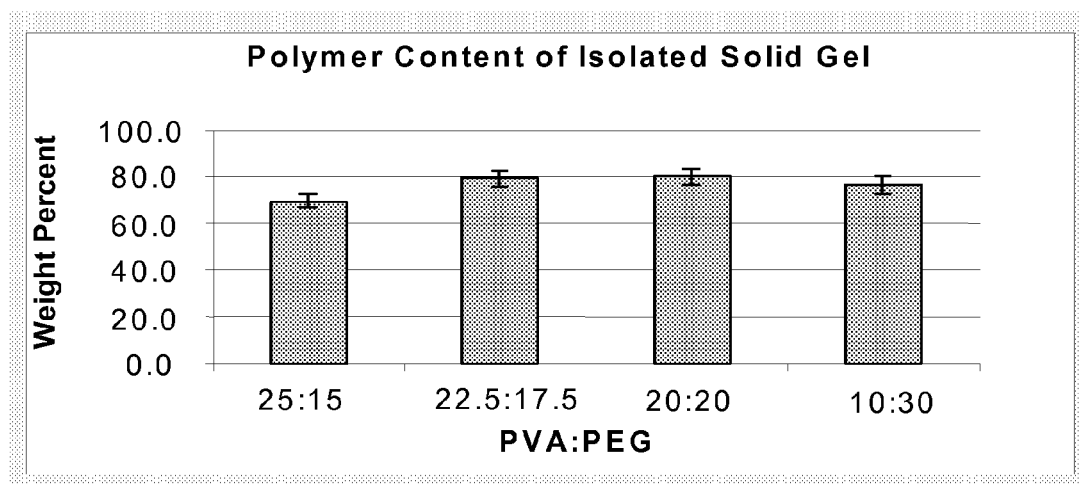
FIG. 4 is a graphical representation of the polymer content of the solid hydrogel at differing ratios of components.

FIG. 4 shows the polymer content in the isolated resultant solid hydrogel. The polymer content was determined by weighing the hydrated resultant hydrogel, drying the water off in an oven, and then weighing the remaining dry polymer material. The polymer content is equal to the final dry mass divided by the wet mass of the hydrated hydrogel.

FIG. 4 demonstrates that the polymer content ranged from approximately 70% to 80% for the solid resultant hydrogel. Accordingly, the water content of the hydrogel was only approximately 20% to 30%. Such a low water content would be difficult to achieve with typical solution making methods, indicating that this method of hydrogel formation may have advantages over other methods described in greater detail below.

Figure 5:
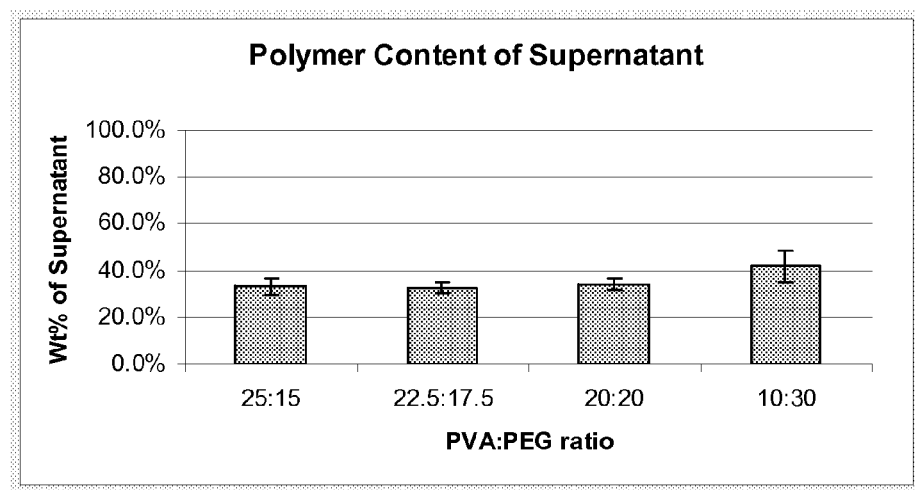
FIG. 5 is a graphical representation of the polymer content of the supernatant at differing ratios of components.

FIG. 5 shows the polymer content of the liquid supernatant phase. The polymer content was calculated as described above. FIG. 5 demonstrates that the polymer content of the supernatant ranges from approximately 33% to 42%. Accordingly, the water content of the supernatant phase, approximately 58% to 67%, was higher than the water content of the hydrogel.

The data in FIGS. 3 through 5 show that this method of hydrogel formation results in a higher polymer content in the resultant hydrogel composition as compared to the polymer content of the precursor polymer solution. Other methods of forming a hydrogel composition may include dissolving the polymer in a solvent at room temperature. For example, the manufacturer's specifications for PVA indicate that the solubility limit is 13% under such conditions. Another method may be dissolving the polymer in a solvent at an elevated temperature under pressure, for example, in an autoclave. One could expect to achieve a polymer content of approximately 28% with this method. The addition of PEG followed by the dehydration allows for the production of a resultant hydrogel composition with a higher polymer content than the precursor polymer solution. Additionally it can be seen that changing the PVA/PEG ratio in the composition may have an effect on the resultant polymer content of the hydrogel, as well as how much of the initial solution separates, and how components of that mixture distribute, between the solid hydrogel or supernatant phases.

Example 5

Preparation of PVA/PVP/PEG Hydrogel Compositions

Resultant PVA/PVP/PEG hydrogel compositions were prepared generally as described in Example 1 for PVA/PEG hydrogels. Briefly, preparation of the hydrogel composition involved the formation of a PVA/PVP solution and a subsequent step wherein PEG was added to the PVA/PVP solution in order to dehydrate the hydrogel and then form the resultant hydrogel and supernatant phases. The resultant dehydrated hydrogel phase was separated from the supernatant waste stream. After the hydrogel component is separated, it was then molded.

More specifically, in a first step, an aqueous solution of PVA (28-99; 99% hydrolyzed; Mw=145,000 Da) and PVP (C-30; Mw=58,000 Da) was prepared in deionized water at a final polymer concentration of 28%, which is sufficient for gelation at room temperature. The solution was prepared at a temperature of between about 87° C. and about 120° C., preferably 95° C. The ratio of PVA to PVP was 99:1.

In this example, Barium Sulfate (1-10 um) was then dispersed into the solution by mixing in order to form a suspension. A 5% to 15% concentration of Barium Sulfate in the resultant hydrogel composition was sufficient to be radiopaque for hydrogels. The addition of Barium Sulfate is an optional step.

In a second step, a precursor polymer solution was prepared by mixing PEG (Mr=10,000 Da) into the PVA/PVP solution while maintaining the solution at a temperature between about 65° C. and about 100° C., preferably about 75° C. The presence of PEG served a dual role as a plasticizer of the hydrogel for injectability, as well as concentrator for increasing the polymer content of the hydrogel. The addition of PEG resulted in a phase separation which resulted in the formation of a supernatant phase which drew water from the hydrogel. The supernatant, consisting of PEG in aqueous solution, was removed and the resultant hydrogel was then molded as described in Example 1.

The concentrations of the components in the precursor polymer solution are provided in Table 4. Table 4 shows the composition at each stage (PVA/PVP solution formation, barium addition and PEG addition).

TABLE 4

Concentrations of Components in the Precursor Polymer Solutions

| Component | Solution Formation | | Addition of Barium | | Addition of PEG | |
| --- | --- | --- | --- | --- | --- | --- |
| | Mass (g) | Composition (%) | Mass (g) | Composition (%) | Mass (g) | Composition (%) |
| PEG | — | — | — | — | 17.7 | 17.7 |
| PVA | 20.1 | 26.7 | 20.1 | 24.4 | 20.1 | 20.1 |
| PVP | 0.2 | 0.3 | 0.2 | 0.2 | 0.2 | 0.2 |
| DI Water | 55.0 | 73.0 | 55.0 | 66.8 | 55.0 | 55.0 |
| Barium Sulfate | — | — | 7.0 | 8.5 | 7.0 | 7.0 |

A mass balance analysis was performed on the resultant hydrogel composition and the liquid supernatant as described above. Solid components were separated from water by mass lost upon drying in an oven at 105° C. Barium Sulfate content was obtained by mass loss on ignition in a furnace at 650° C. PVA and PEG were separated using nuclear magnetic resonance spectroscopy (NMR), where the location of chemical functional groups on each PVA and PEG gave an indication of the mass of each material in a blended polymer sample. Table 5 shows the composition of the resultant hydrogel compositions.

TABLE 5

Concentration of Components of the
Resultant Hydrogel Composition

| Phase | Composition of Total (% w/w) | Component | Composition per Phase (% w/w) |
|---|---|---|---|
| Solid Hydrogel | 66.6 | PEG | 6.5 |
| | | PVA | 33.8 |
| | | PVP | 0.3 |
| | | DI Water | 47.9 |
| | | Barium Sulfate | 11.5 |
| Aqueous Supernatant | 33.4 | PEG | 37.8 |
| | | PVA | — |
| | | PVP | — |
| | | DI Water | 62.2 |
| | | Barium Sulfate | — |

Example 6

Differential Scanning Calorimetry Analysis

To characterize phase transitioning behavior of the resultant hydrogel, DSC experiments were performed on two sample compositions. The first sample was the resultant PVA/PVP/PEG hydrogel composition formulated as described in Example 5. The resultant hydrogel composition was equilibrated at 25° C. and then heated at a rate of 5° C./min to 120° C. The second sample was a control composition of a PVA/PVP hydrogel (i.e., without the PEG). The ratios of the remainder of the components were the same as with the PVA/PVP/PEG hydrogel.

Figure 6:
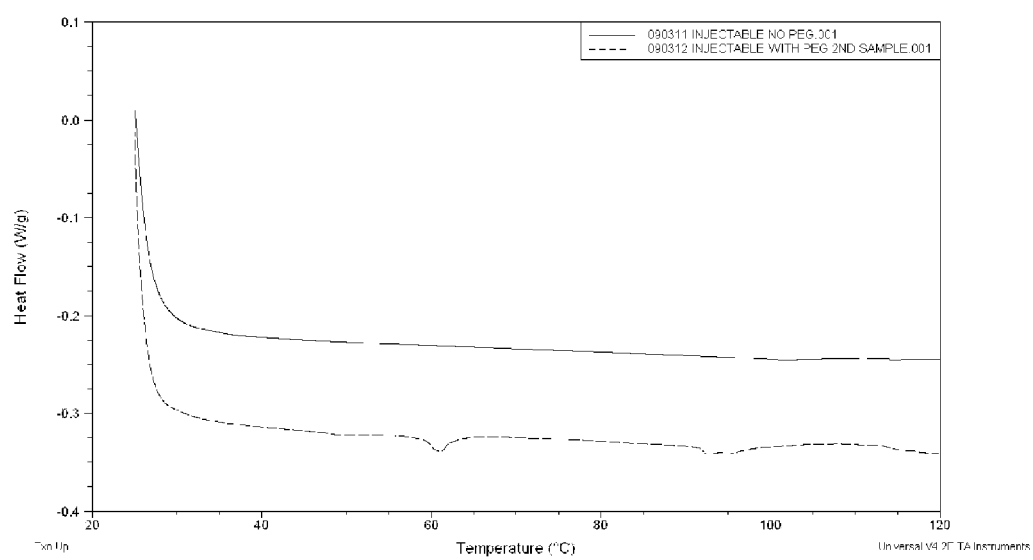
FIG. 6 is a graphical representation of the differential scanning calorimetry thermograms for hydrogel compositions with PEG (dashed line) and without PEG (solid line).

FIG. 6 shows the resultant PVA/PVP/PEG hydrogel composition (dashed line) and the control composition (solid line). Two melt transitions were observed in the resultant PVA/PVP/PEG hydrogel composition and no transitions were observed in the control composition. At approximately 60° C., there is a melt transition present in the resultant hydrogel composition that contains PEG, but not in the hydrogel composition without PEG. Additionally, there is a melt transition at 90° C. to 95° C. for the PEG containing hydrogel composition. There is a slight endotherm for the hydrogel composition without PEG at a slightly higher temperature, approximately 100° C. The presence in the PEG containing hydrogel composition of a melt transition at 60° C., which is in the range of the melting temperature of PEG (i.e, approximately 60° C.), indicates that the PEG is in melt form, not solution (i.e., a solvent and soluent), as that temperature is associated with PEG melting, not PEG solution melting. The 90° C. to 95° C. melt transition is in the range of the temperature required for the hydrogel to be melted and become flowable for delivery.

Example 7

Parallel Plate Rheometric Analysis

Parallel plate rheometry was utilized in order to determine the viscoelastic characteristics of the resultant hydrogel composition across a range of processing and delivery temperatures. Resultant hydrogel composition samples (n=4), as prepared in Example 5, were tested between two parallel plates having a plate gap of 0.750 mm which oscillate in torsion at 1 Hz for 0.5% strain. The test yielded viscosity and elasticity modulus data for the resultant hydrogel composition samples and provided insight into the viscoelastic behavior of the compositions. A Peltier plate heating system allowed the resultant hydrogel composition samples to be analyzed at a range of temperatures.

Figure 7:
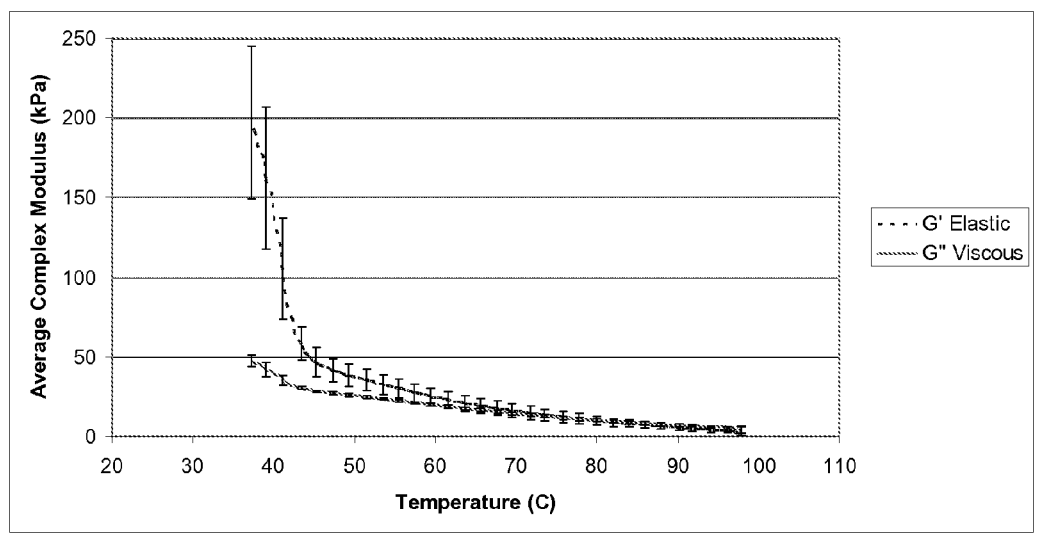
FIG. 7 is a graphical representation of the average complex modulus (i.e., storage and loss).

The test was designed using this rheometer setup to mimic the in vivo cooling of the PEG-containing resultant hydrogel composition once implanted into a patient. In this test, the resultant hydrogel composition was heated to 95° C. to remove any physical associations between the polymers in the hydrogel, and then subjected to a controlled cool over twenty minutes, to 37° C. The relative contribution of elastic and viscous effects was described by using the elastic (storage or G') and viscous (loss or G") moduli, respectively. FIG. 7 shows the average complex modulus (i.e., storage and loss) across a range of temperatures. A steep increase in the elastic modulus (storage or G') component was observed at lower temperatures (i.e., below 45° C.). This sharp increase was similar to what was observed for the viscosity measurements in FIG. 9 with the same hydrogel composition samples. Solidification was exhibited at 45° C., which enabled a low working temperature, improving workability (i.e., injectability and/or flowability) of the resultant hydrogel composition for delivery via injection. The location of the transition temperature was advantageous in that this is close to physiological temperature, between about 29° C. and about 40° C. The sharp increase in elasticity demonstrated in FIG. 7 at about 45° C. is unexpected. One would have expected a gradual increase in elasticity as the temperature decreased such as that demonstrated in FIG. 8 for the control samples.

The temperature at the crossover point of the elastic (storage or G') and viscous (loss or G") modulus is defined in ASTM D4473 as the gel point (ASTM 04473-08 Standard Test Method for Plastics: Dynamic Mechanical Properties: Cure Behavior). This gel point is considered to be the point where the elastic and viscous components diverge. This occurred at approximately 60° C. for PEG-containing resultant hydrogel compositions (See FIG. 7).

Figure 8:
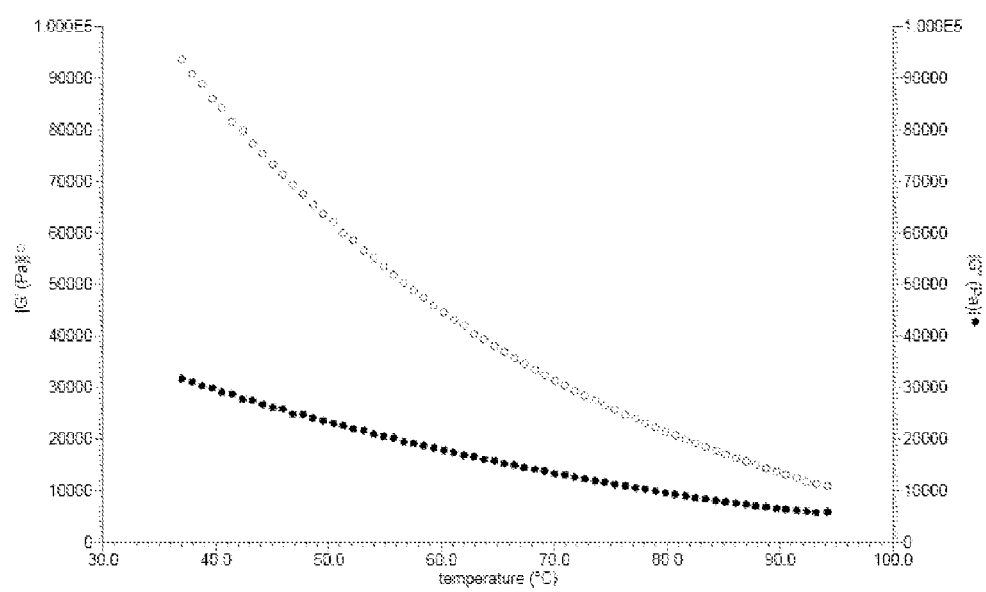
FIG. 8 is a graphical representation of the storage (G'; hollow circles) and loss (G"; solid circles) moduli.

FIG. 8 shows the results for hydrogel compositions lacking PEG. The elastic modulus (storage or G') was greater than the viscous modulus (loss or G") at all temperatures examined (i.e., in the range of about 35° C. and about 95° C.), indicating that the material was below its gel point at all working temperatures (i.e., up to approximately 80° C.), and thus a gel at all times. This indicated that the composition lacking PEG was less flowable than the PEG-containing hydrogel composition.

Example 8

Viscosity Analysis

Figure 9:
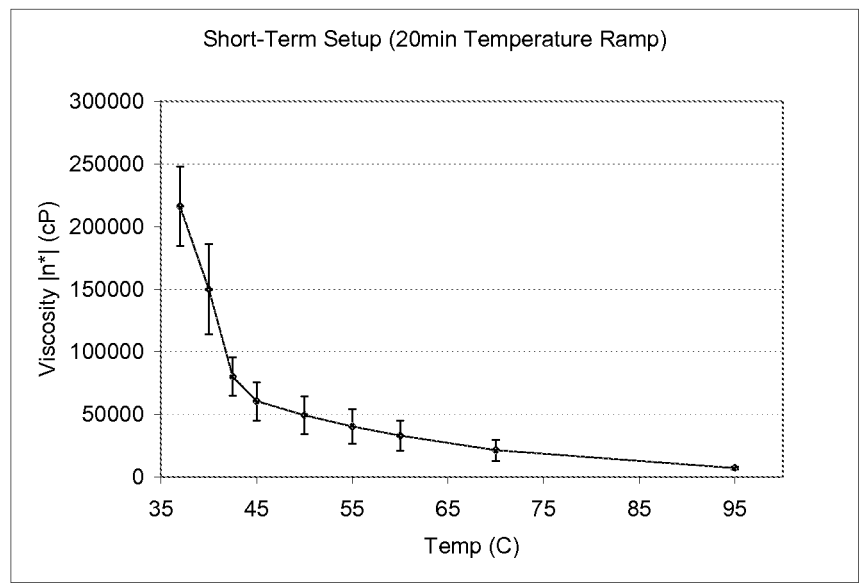
FIG. 9 is a graphical representation of the viscosity properties of PVA/PVP/PEG hydrogel compositions.

Viscosity data was obtained using test conditions as described in more detail in Example 7. Resultant PVA/PVP/PEG hydrogel composition samples (n=4) were prepared as described in Example 5. Control samples (n=4) without PEG were also tested. The change in viscosity over changes in temperature from this test is shown in FIG. 9. The temperature was ramped up over 20 minutes from 37° C. to 95° C. (i.e., Short-Term Setup (20 min Temperature Ramp)). The PEG-containing hydrogel composition was observed to undergo a transition at approximately 45° C. that resulted in an increase in viscosity at between about 37° C. and about 45° C. The viscosity measurement is a measure of complex viscosity, as denoted by the "|n*|" symbol. The units are expressed as centipoise (cP).

Figure 10:
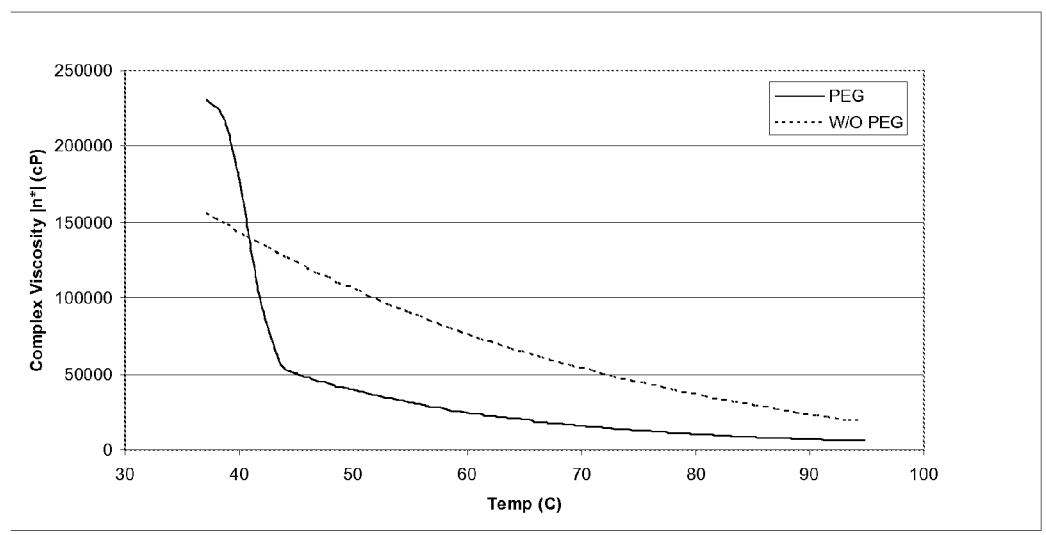
FIG. 10 is a graphical representation of the viscosity properties of a PEG-containing hydrogel composition (solid line) in comparison to a hydrogel composition lacking PEG (dashed line).

The effect of the inclusion of PEG in the hydrogel composition on the final viscosity is depicted in FIG. 10. A representative viscosity curve for the resultant PEG containing hydrogel composition is shown as a solid line. The control hydrogel composition lacking PEG is shown as a dashed line. The injection viscosity (T>42° C.) is lower for samples containing PEG, as compared to those samples without PEG.

Example 9

Mechanical Testing

Figure 11:
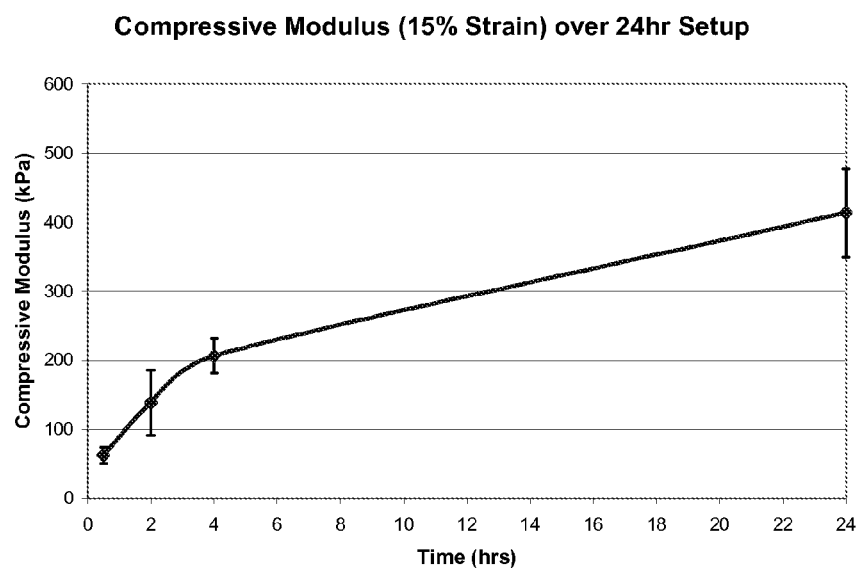
FIG. 11 is a graphical representation of compressive modulus of a resultant hydrogel composition at 15% strain over 24 hours.

Cylinders of the resultant hydrogel composition (n=4), prepared as in Example 5, were molded and tested axially in compression. Each resultant hydrogel composition was stored sealed in the mold at 37° C. in a humid environment until time of testing. FIG. 11 shows the compressive modulus (expressed as chord modulus at 15% strain). Modulus, obtained for 0.5, 2, 4 and 24 hour time points, increased steadily throughout the experiment, indicating that the hydrogel composition became a stiffer and more elastic gel over time.

Example 10

Osmotic Swelling and Stability Analysis

The osmotic pressure of the intervertebral disc ranges from approximately 0.1 to approximately 0.3 Mega Pascals (MPa). Accordingly, it would be advantageous for the resultant hydrogel composition to maintain volume or swell in osmotic environments higher than approximately 0.1 MPa. The resultant PEG-containing hydrogel composition, as prepared in Example 5, was placed in PEG solutions of differing concentrations. PEG solutions are known to have predictable osmotic pressures, so solutions with specific concentrations of PEG can be made resulting in a range of osmotic pressures. The change in volume in an unconstrained environment (i.e., wherein nothing is touching or constraining the hydrogel, thus, it is free to swell) can then be determined to determine how the hydrogel composition would respond in different osmotic environments. The volume of PEG solution was sufficient to allow "sink" conditions (i.e., the volume of PEG liquid is in such excess that the osmotic pressure won't change when water comes out of the gel), where the ratio of volume of solution to mass of hydrogel composition was approximately 35:1. The solutions were maintained at 37° C. for 7 days.

Figure 12:
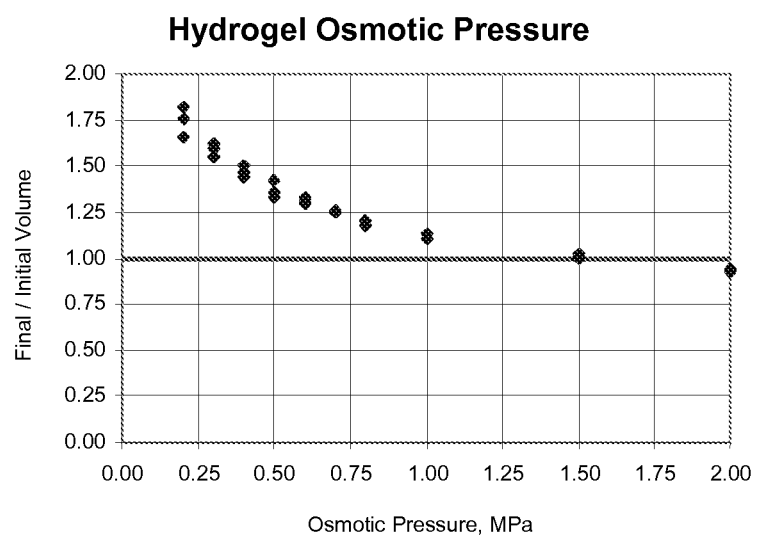
FIG. 12 is a graphical representation of the osmotic pressure of a resultant hydrogel composition.

FIG. 12 shows the change in volume (final/initial volume) versus the osmotic pressure the hydrogel composition was placed in. When the final/initial volume reaches 1, the volume is not changing, indicating the osmotic pressure of the hydrogel composition. As can be seen from the graph of FIG. 12, the osmotic pressure of the hydrogel composition is approximately 1.5 MPa. An osmotic pressure of 1.5 MPa means that in an environment with an osmotic pressure lower than 1.5 MPa, the hydrogel composition will swell and in an environment with an osmotic pressure higher than 1.5 MPa, the hydrogel composition will shrink. So, in the osmotic environment of the disc, 0.1-0.3 MPa, the resultant hydrogel composition would be expected to swell.

Figure 13:
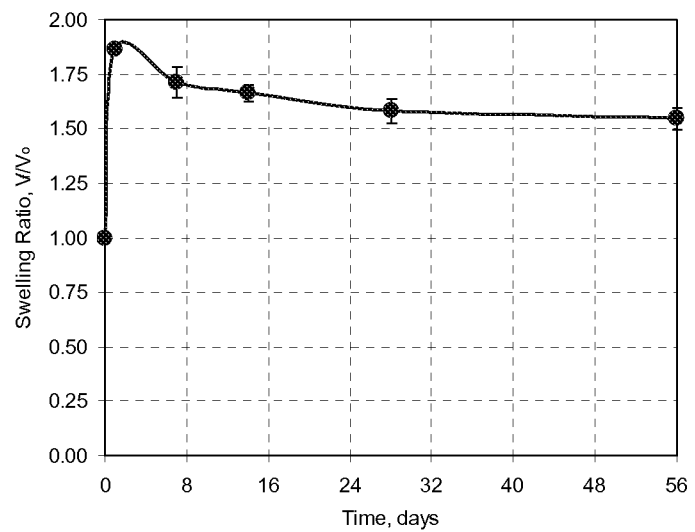
FIG. 13 is a graphical representation of the swelling of a resultant hydrogel composition in 0.2 MPa solution over 56 days.
Figure 14:
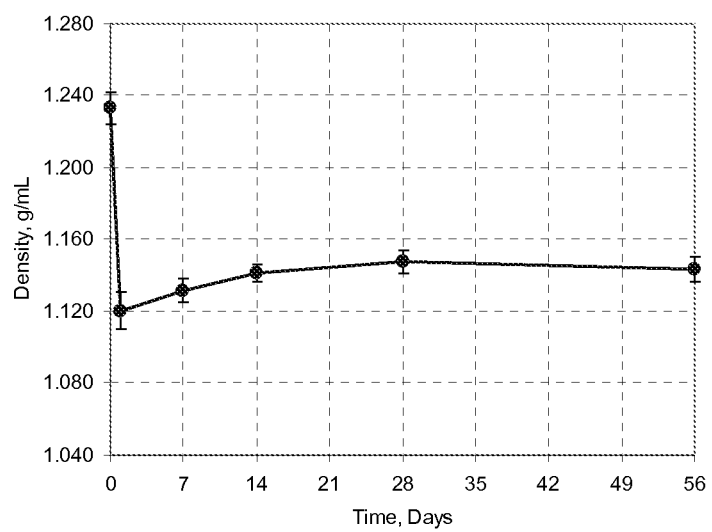
FIG. 14 is a graphical representation of the density of a resultant hydrogel composition in a 0.2 MPa osmotic solution over 56 days.
Figure 15:
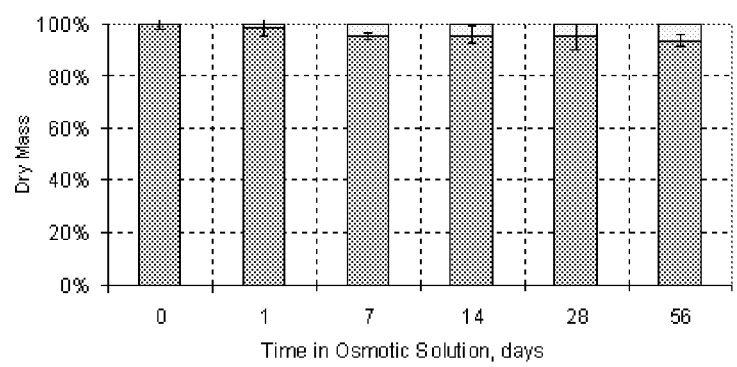
FIG. 15 is a graphical representation of the dry mass stability of a resultant hydrogel composition over 56 days immersion in 0.2 MPa osmotic solution.

Further tests were performed by placing another resultant hydrogel composition sample, prepared as in Example 5, in a 0.2 MPa solution in sink conditions to determine the unconstrained swelling of the material and the dry mass stability. Swelling was measured at different time points by observing changes in the volume and density of the resultant hydrogel composition. Dry mass stability is a measure of how much of the original dry mass of the hydrogel composition (not including water) remains with the hydrogel composition after immersion and indicates how stable the hydrogel composition would be in this osmotic environment. FIGS. 13, 14, and 15 show the swelling ratio, density, and dry mass retention versus immersion time, respectively.

FIG. 13 indicates that the swelling ratio, measured as a ratio of resulting volume (V) to initial volume ($V_o$), leveled off at just above 1.5 by the 56 day time point. A swelling ratio of greater than one indicated that the hydrogel composition pulled in water and increased in volume.

FIG. 14 indicates a decrease in density which leveled off at about 1.15 g/ml. This decrease in density was also an indication that the hydrogel composition pulled in water, and was another indication of the swelling of the hydrogel composition.

FIG. 15 indicates the resultant hydrogel composition maintained approximately 95% of its original dry mass when immersed in the 0.2 MPa solution for 56 days. The dry mass percentage seemed to have leveled off which may indicate that the resultant hydrogel composition reached its equilibrium state and was no longer changing. The conclusion from the swelling and stability tests was that the resultant hydrogel composition does swell, but was stable in sink conditions that simulate the disc osmotic environment.

Example 11

Viscosity Analysis for Compositions of Varying Component Concentrations

To determine the effect of varying the component concentrations in the resultant hydrogel composition, five sample resultant hydrogel compositions were prepared (i.e., Samples A through E) and then subjected to viscosity analyses as described herein above. The concentrations (% w/w) of the components in the precursor polymer solutions are provided in Table 6. A constant total polymer concentration was maintained in the precursor polymer solutions. Thus, even though the individual polymer components in the precursor polymer solutions were varied, the total polymer content in the precursor polymer solutions remained the same.

TABLE 6

Concentrations of the Components of the Precursor Polymer Solutions

| | Sample Compositions | | | | |
|---|---|---|---|---|---|
| | A | B | C | D | E |
| PEG (10 kDa) | 12.73% | 14.73% | 17.73% | 20.73% | 22.73% |
| PVA (Mowiol 28-99) | 25.06% | 23.06% | 20.06% | 17.06% | 15.06% |
| PVP (Plasdone C-30) | 0.20% | 0.20% | 0.20% | 0.20% | 0.20% |
| Deionized Water | 55.00% | 55.00% | 55.00% | 55.00% | 55.00% |
| Barium Sulfate | 7.00% | 7.00% | 7.00% | 7.00% | 7.00% |

A mass balance analysis was performed on the resulting sample hydrogel compositions as described in Example 5. The results are shown in Table 7. The "% solids" represents the total amount of solid components after the supernatant was decanted from the solid hydrogel and the liquid had been dried off of the hydrogel. The "% solids" also included the Barium Sulfate.

TABLE 7

Resultant Hydrogel Composition Concentrations

| | Sample Compositions | | | | |
|---|---|---|---|---|---|
| | A | B | C | D | E |
| PEG | 9.1% | 8.5% | 6.5% | 7.7% | 10.6% |
| PVA | 31.8% | 29.2% | 33.5% | 40.5% | 33.8% |
| PVP | 0.3% | 0.3% | 0.3% | 0.4% | 0.3% |
| Deionized Water | 52.2% | 51.9% | 47.9% | 40.7% | 43.4% |
| Barium Sulfate | 6.7% | 10.1% | 11.5% | 10.7% | 11.9% |
| % Solids | 47.8% | 48.1% | 52.1% | 59.3% | 56.6% |
| % Polymers | 41.1% | 38.0% | 40.6% | 48.6% | 44.7% |

Figure 16:
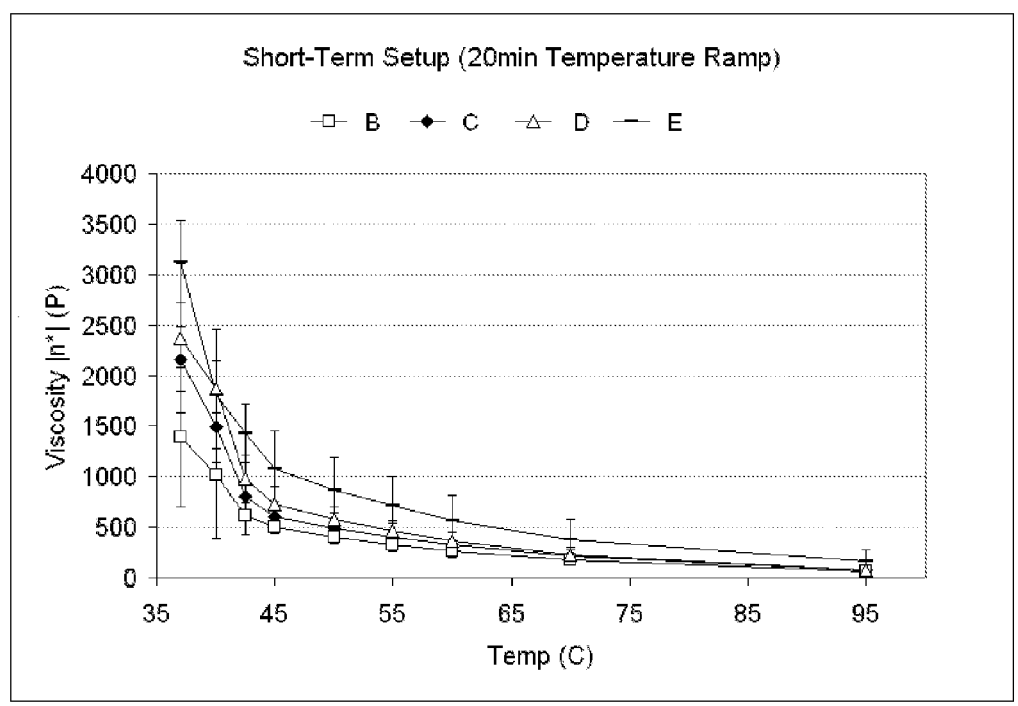
FIG. 16 is a graphical representation of the viscosities of resultant hydrogel compositions of varying PEG concentrations at varying temperatures.

The viscosity data was obtained using a parallel plate rheometer in oscillatory shear as described in greater detail in Example 8. Each data point consisted of four samples from each sample composition (e.g., four Sample A compositions). FIG. 16 shows the viscosities measured for sample compositions B, C, D and E at temperatures ranging from 37° C. to 95° C. At any given temperature, the hydrogel compositions with a higher PEG concentration exhibited greater viscosity.

Figure 17:
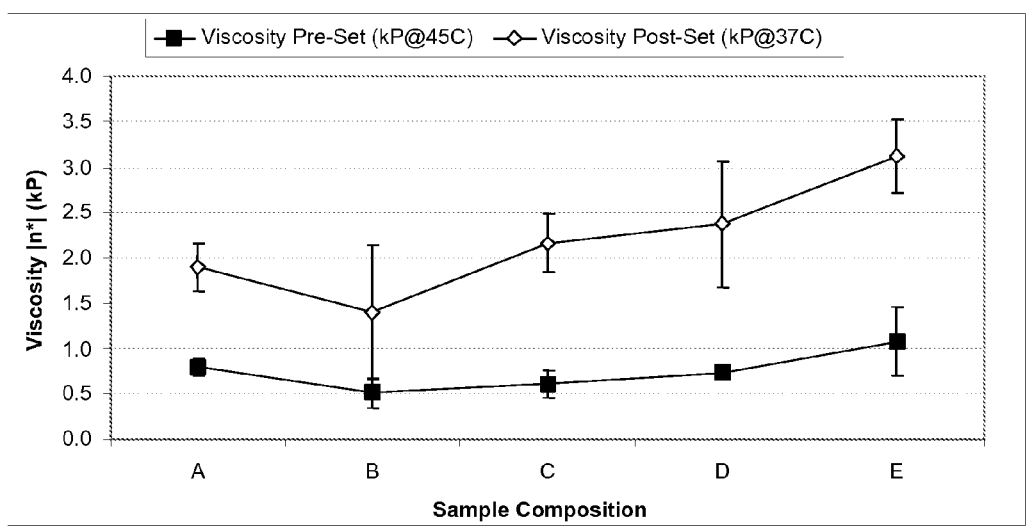
FIG. 17 is a graphical representation of the viscosities of resultant hydrogel compositions of varying PEG concentrations at pre-setting and post-setting temperatures.

Viscosity measurements were also taken at pre-setting and post-setting temperatures. Samples were held at 95° C. for 5 minutes, then cooled over 20 minutes to 37° C. to evaluate viscosity at temperatures before cure onset ("pre-setting") (i.e., greater than 45° C.) as well as at setting temperature ("post-setting") (i.e., 37° C.). FIG. 17 shows that for all of the sample resultant hydrogel compositions, the post-setting samples had a higher viscosity than the pre-setting samples. The difference between post-setting and pre-setting viscosity was greatest for samples with greater amounts of PEG in the precursor polymer solution. As the post-setting viscosity increased, so did the pre-setting viscosity.

All of the sample compositions were capable of being injected from a delivery gun using a 2.5 mm ID cannula (i.e., the "Hydrafil cannula") after internally heating the sample compositions to 95° C. for five minutes.

For samples with a lower concentration of PEG in the precursor polymer solution, the water content in the resultant hydrogel was high, which may decrease the post-setting viscosity. Pre-setting viscosity for these resultant hydrogel samples was high due to increased PVA concentration.

Example 12

Figure 18:
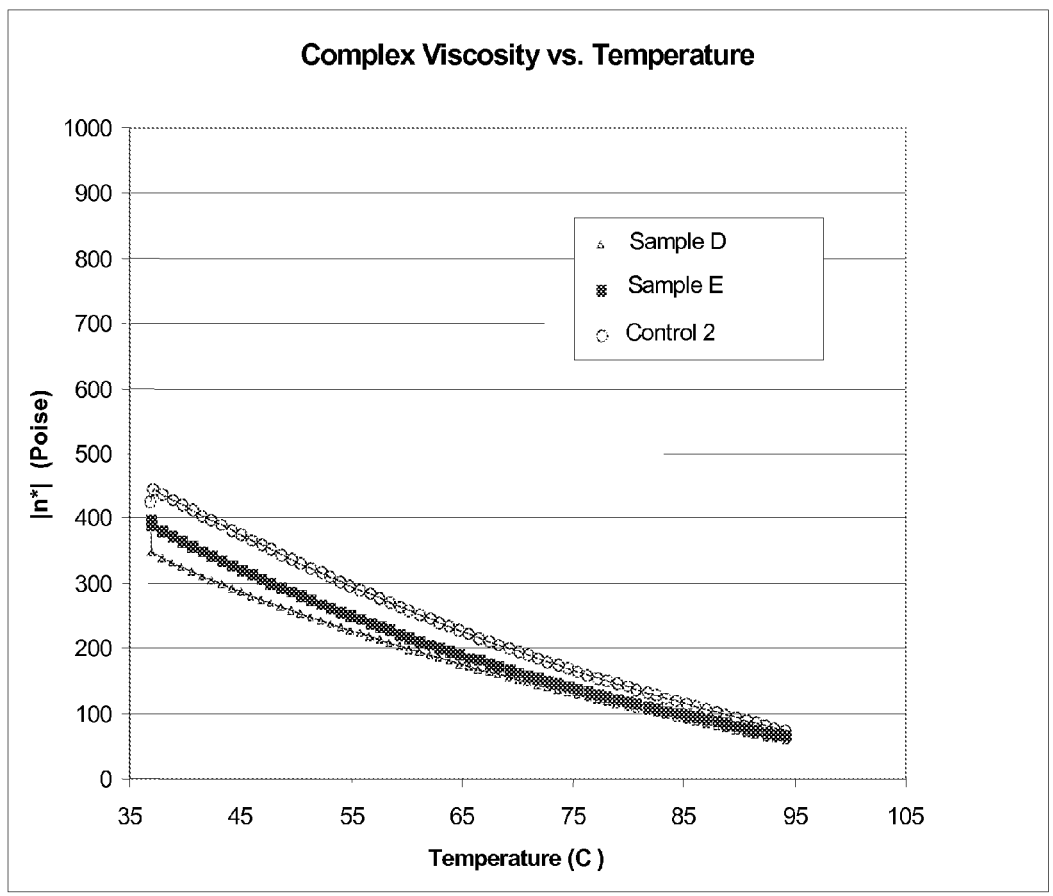
FIG. 18 is a graphical representation of the complex viscosities at varying temperatures of resultant hydrogel compositions resulting from varying PEG concentrations in the precursor polymer solution.

Viscosity Analysis of Resultant Hydrogel Compositions Resulting from Varying PEG Concentrations in the Precursor Polymer Solution To determine the effect of varying the PEG concentrations in the precursor polymer solution, five sample resultant hydrogel compositions (n=3) were prepared (i.e., Samples A through E) and then subjected to viscosity analyses as described herein above. Two control samples (i.e., Control 1 and Control 2) (n=3) were also prepared. The quantities (mmol) of the components in the precursor polymer solutions are provided in Table 8.

each sample/control composition (e.g., three Sample A compositions). FIG. 18 shows the viscosity measurements at different temperatures for Control 2 and Samples D and E. The viscosity measurement is a measure of complex viscosity, as denoted by the "|n*|" symbol. Control 2, with no PEG in the precursor polymer solution and Sample E, with 0.000797 mmol of PEG in the precursor polymer solution, did not form a supernatant and exhibited a steady increase in viscosity as the temperature was lowered. Sample D, with 0.00159 mmol of PEG in the precursor polymer solution, did form a supernatant and also exhibited the steady increase in viscosity as the temperature was lowered. However, Sample D showed a slight upturn at the lowest temperature measured, 37° C.

Figure 19:
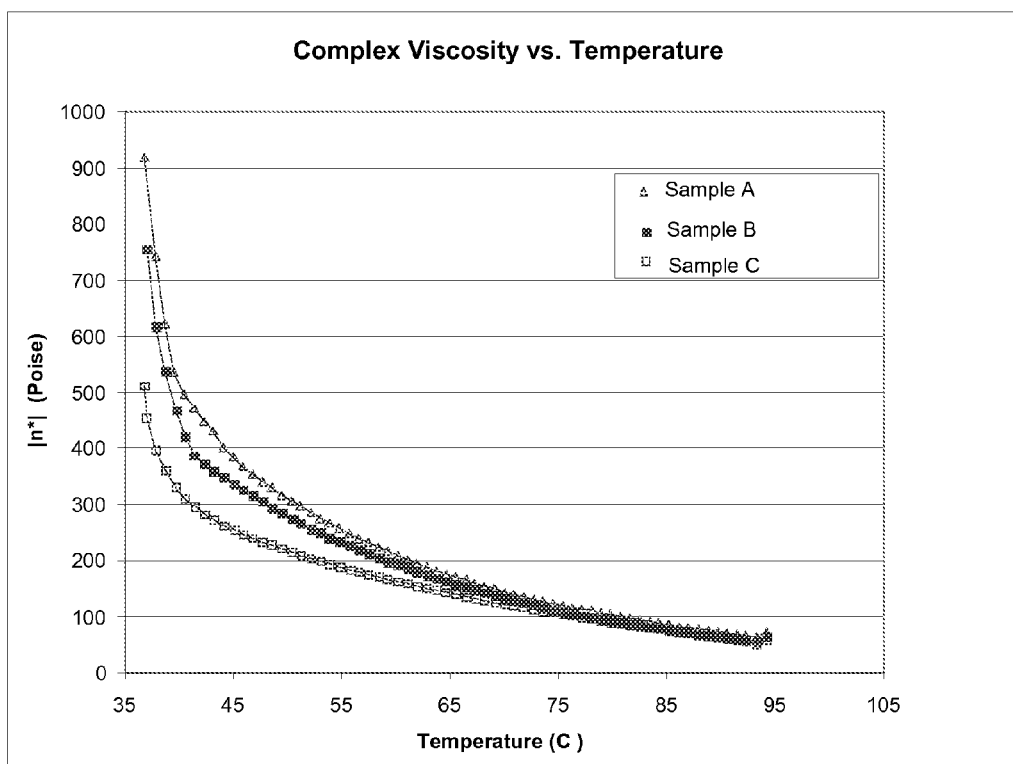
FIG. 19 is a graphical representation of the complex viscosities at varying temperatures of resultant hydrogel compositions resulting from varying PEG concentrations in the precursor polymer solution.

FIG. 19 shows the viscosity measurements at different temperatures for Samples A, B and C, which all formed a supernatant. Similar to the observations in FIG. 16, Samples A, B and C exhibited a sharp increase in viscosity at lower temperatures which was not observed in the Control 2, Sample D or Sample E. See FIG. 18.

Figure 20:
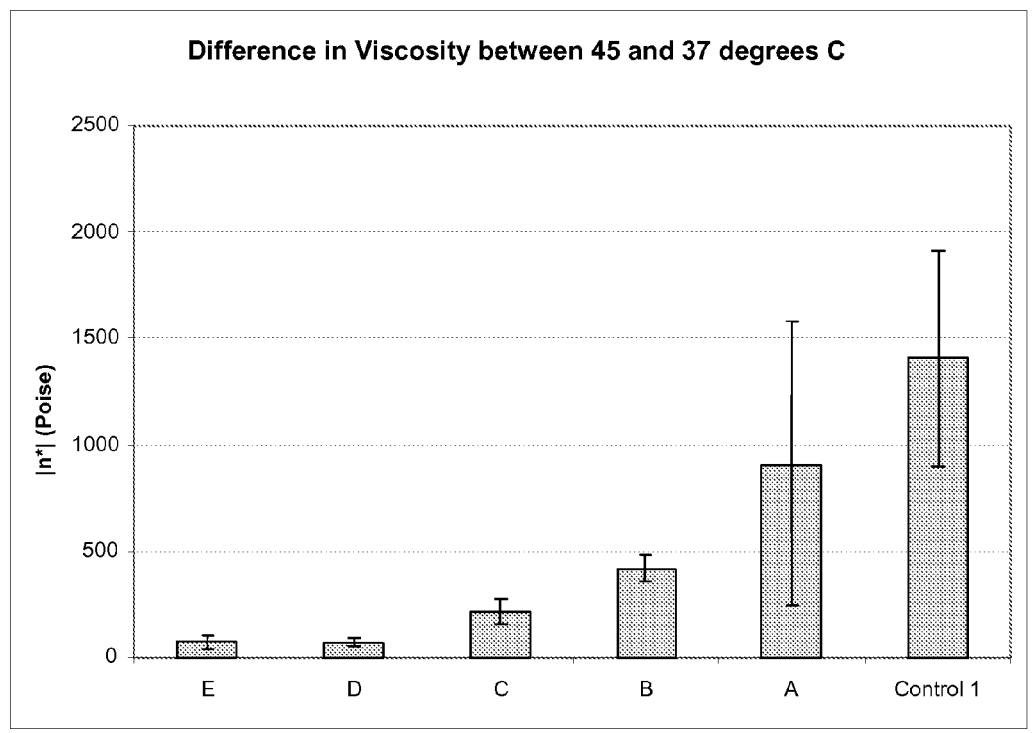
FIG. 20 is a graphical representation of the difference in viscosities measured at 45° C. and 37° C. of resultant hydrogel compositions resulting from varying PEG concentrations in the precursor polymer solution.

FIG. 20 shows the difference between viscosities measured at 45° C. and 37° C. (i.e., viscosity at 45° C. minus the viscosity at 37° C.), which is indicative of the observed setting behavior (i.e., the formation of a supernatant and the resultant hydrogel composition). Generally, greater amounts of PEG in the precursor polymer solution correlated with a larger increase in viscosity. Control 1, which has the same amount of PEG as Sample A, but also includes PVP, showed the highest viscosity.

Figure 21:
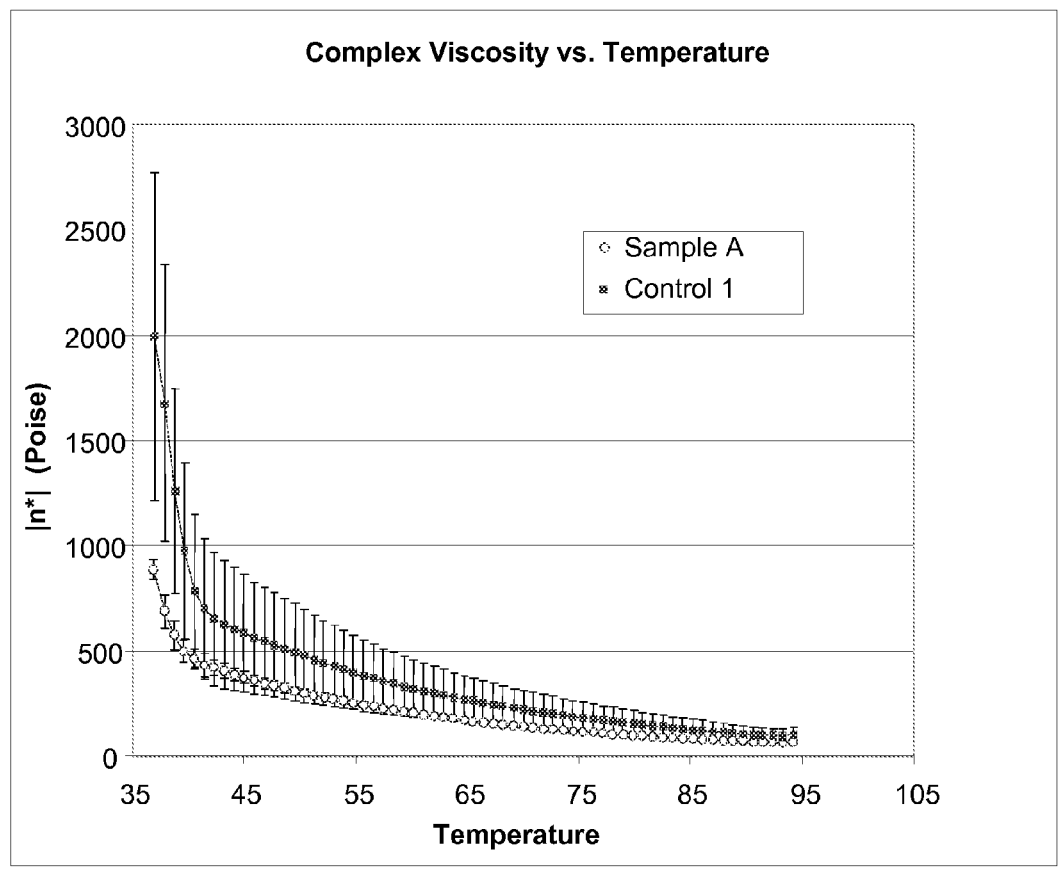
FIG. 21 is a graphical representation of the complex viscosities at varying temperatures of resultant hydrogel compositions resulting from varying PEG concentrations in the precursor polymer solution.

FIG. 21 shows the viscosity measurements at different temperatures for Samples A and Control 1. Control 1 exhibited a higher viscosity at lower temperatures than Sample A.

Example 13

Viscosity Analysis of Resultant Hydrogel Compositions Resulting from Varying Water Concentrations in the Precursor Polymer Solution To determine the effect of varying the water concentrations in the precursor polymer solution, five sample resultant hydrogel compositions (n=3) were prepared (i.e., Samples A through E) and then subjected to viscosity analyses as described above. One control sample (n=3) was also prepared. The quantities (mmol) of the components in the pre-

TABLE 8

Quantities (mmol) of the Components of the Precursor Polymer Solutions

| Component | Control 1 | Control 2 | Sample A | Sample B | Sample C | Sample D | Sample E |
|---|---|---|---|---|---|---|---|
| PEG (10 kDa) | 0.0177 | 0 | 0.0177 | 0.0142 | 0.0071 | 0.00159 | 0.000797 |
| PVA (Mowiol 28-99) | 0.00138 | 0.00138 | 0.00138 | 0.00138 | 0.00138 | 0.00138 | 0.00138 |
| Deionized Water | 30.5 | 30.5 | 30.5 | 30.5 | 30.5 | 30.5 | 30.5 |
| PVP (Plasdone C-30) | 0.0000345 | 0 | 0 | 0 | 0 | 0 | 0 |
| Barium Sulfate | 0.3 | 0 | 0 | 0 | 0 | 0 | 0 |

The viscosity data was obtained using a parallel plate rheometer in oscillatory shear as described in greater detail in Example 8. Each data point consisted of three samples from cursor polymer solutions are provided in Table 9. Also provided in Table 9 is the water concentration in the resultant hydrogel composition for each sample.

TABLE 9

Quantities (mmol) of the Components of the Precursor Polymer Solutions

| | Control 1 | Sample A | Sample B | Sample C | Sample D | Sample E |
|---|---|---|---|---|---|---|
| DI Water | 30.5 | 53.4 | 38.2 | 30.5 | 22.9 | 19.8 |
| PEG (10 kDa) | 0.0177 | 0.0177 | 0.0177 | 0.0177 | 0.0177 | 0.0177 |
| PVA (Mowiol 28-99) | 0.00138 | 0.00138 | 0.00138 | 0.00138 | 0.00138 | 0.00138 |

TABLE 9-continued

Quantities (mmol) of the Components of the Precursor Polymer Solutions

|  | Control 1 | Sample A | Sample B | Sample C | Sample D | Sample E |
|---|---|---|---|---|---|---|
| PVP (Plasdone C-30) | 0.0000345 | 0 | 0 | 0 | 0 | 0 |
| Barium Sulfate | 0.3 | 0 | 0 | 0 | 0 | 0 |
| Water Concentration (% w/w) in Resultant Hydrogel Composition | N/A | 62.4% | 55.9% | 49.2% | 43.6% | 40.8% |

Figure 22:
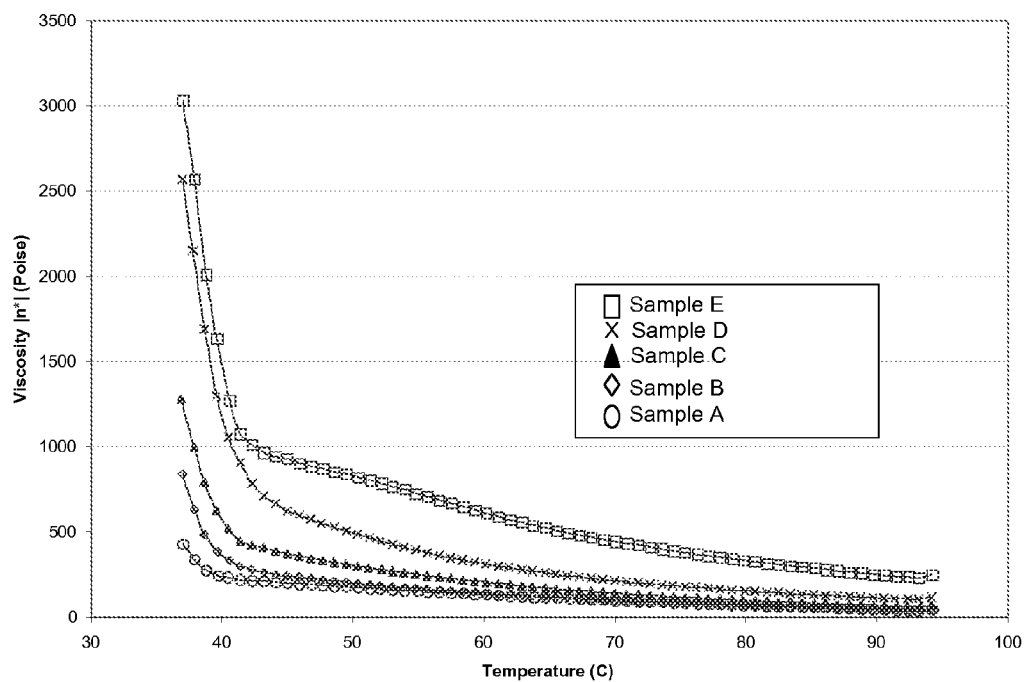
FIG. 22 is a graphical representation of the complex viscosities at varying temperatures of resultant hydrogel compositions resulting from varying water concentrations in the precursor polymer solution.

The viscosity data was obtained using a parallel plate rheometer in oscillatory shear as described in greater detail in Example 8. Each data point consisted of three samples from each sample/control composition (e.g., three Sample A compositions). FIG. 22 shows the viscosity measurements at different temperatures for Samples A through E. The viscosity measurement is a measure of complex viscosity, as denoted by the "|n*|" symbol. FIG. 22 indicates the inverse relationship between the viscosity and the water content in the resultant hydrogel composition. The less water in the precursor polymer solution, the less water in the resultant hydrogel composition and the higher viscosity at all temperatures tested.

Figure 23:
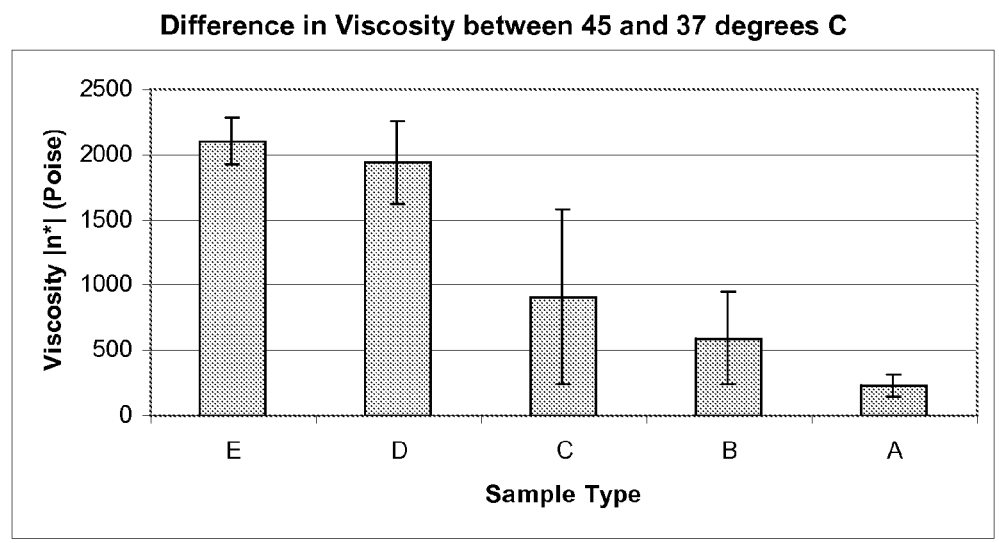
FIG. 23 is a graphical representation of the difference in viscosities measured at 45° C. and 37° C. of resultant hydrogel compositions resulting from varying water concentrations in the precursor polymer solution.

FIG. 23 shows the difference between viscosities measured at 45° C. and 37° C. (i.e., viscosity at 45° C. minus the viscosity at 37° C.), which is indicative of the observed setting behavior (i.e., the formation of a supernatant and the resultant hydrogel composition). Generally, greater amounts of water in the precursor polymer solution correlated with an increase in viscosity.

The embodiments set forth above, among those made apparent from the preceding description, are efficiently attained and, since certain changes may be made in carrying out the above method of forming and in the resulting composition without departing from the spirit and scope of the invention, it is intended that all material contained in the above description shall be interpreted as illustrative and not in a limiting sense.

It will also be understood that the embodiments presented herein are intended to cover all of the generic and specific features of the composition herein described and all statements of the scope of the invention which, as a matter of language, might be said to fall therebetween. Particularly it is to be understood that in said embodiments, ingredients or compounds recited in the singular are intended to include compatible mixtures of such ingredients.

It will be appreciated by those skilled in the art that changes could be made to the embodiments described above without departing from the broad inventive concept thereof It is understood, therefore, that this invention is not limited to the particular embodiments disclosed, but is intended to cover modifications within the spirit and scope of the present invention as defined by the appended claims.

The invention claimed is:

1. A hydrogel composition comprising polyvinyl alcohol having a molecular weight of about 145,000 Da mixed together with water and polyethylene glycol, and separated into a solid phase and a liquid supernatant phase, wherein the solid phase comprises a total polymer content of about 70% to about 80% by weight of the solid phase and water in an amount of about 20% to about 30% by weight of the solid phase, wherein the liquid supernatant phase comprises a total polymer content of about 33% to about 42% by weight of the liquid supernatant phase and water in an amount of about 58% to about 67% by weight of the liquid supernatant phase, and wherein the total polymer content in the solid phase comprises about 20% to about 65% by weight of polyvinyl alcohol and about 2% to about 20% by weight of polyethylene glycol, wherein the hydrogel composition has a compressive chord modulus of about 450 kPa to about 5,000 kPa.

2. The hydrogel composition of claim 1, wherein the composition further comprises polyvinyl pyrrolidone mixed together with the polyvinyl alcohol, water, and polyethylene glycol, and wherein the total polymer content in the solid phase comprises about 0.10% to about 0.75% by weight of polyvinyl pyrrolidone.

3. The hydrogel composition of claim 1, wherein the hydrogel composition has an osmotic pressure of at least 0.1 MPa.

4. The hydrogel composition of claim 1, wherein the hydrogel composition has a compressive chord modulus of about 450 kPa to about 2,500 kPa.

5. The hydrogel composition of claim 1, wherein the hydrogel composition has a viscosity at 45° C. of about 0.02 kP to about 2.0 kP.

6. The hydrogel composition of claim 1, wherein the hydrogel composition has a viscosity at 37° C. of at least 0.475 kP.

7. The hydrogel composition of claim 1, wherein the composition further comprises a radiopaque component mixed together with the poly(vinyl alcohol), water, and polyethylene glycol.

8. The hydrogel composition of claim 7, wherein the radiopaque component is barium sulfate.

9. A hydrogel composition comprising polyvinyl alcohol having a molecular weight of about 145,000 Da mixed together with water and polyethylene glycol, the hydrogel composition formulated by first preparing and heating an aqueous solution of polyvinyl alcohol, then adding the polyethylene glycol to form a precursor polymer solution, cooling the precursor polymer solution, and allowing a phase separation to occur, thereby producing the hydrogel composition comprising a solid phase and a liquid supernatant phase, wherein the solid phase comprises a total polymer content of about 70% to about 80% by weight of the solid phase and water in an amount of about 20% to about 30% by weight of the solid phase, wherein the liquid supernatant phase comprises a total polymer content of about 33% to about 42% by weight of the liquid supernatant phase and water in an amount of about 58% to about 67% by weight of the liquid supernatant phase, and wherein the total polymer content in the solid phase comprises about 20% to about 65% by weight of polyvinyl alcohol and about 2% to about 20% by weight of polyethylene glycol, and optionally removing the liquid supernatant phase, wherein the hydrogel composition has a compressive chord modulus of about 450 kPa to about 5,000 kPa.

10. The hydrogel composition of claim 9, wherein the composition further includes polyvinyl pyrrolidone, and the polyvinyl pyrrolidone is mixed together with the aqueous solution of polyvinyl alcohol prior to heating the aqueous solution.

11. The hydrogel composition of claim 10, wherein the total polymer content in the solid phase comprises about 0.10% to about 0.75% by weight of polyvinyl pyrrolidone.

12. The hydrogel composition of claim 9, wherein the precursor polymer solution comprises a ratio of polyvinyl alcohol to polyethylene glycol of about 1:10 to about 20:1.

13. The hydrogel composition of claim 10, wherein the precursor polymer solution comprises a ratio of polyvinyl alcohol to polyethylene glycol of about 1:10 to about 20:1.

14. The hydrogel composition of claim 9, wherein the total polymer content in the solid phase comprises about 29% to about 35% by weight of polyvinyl alcohol.

15. The hydrogel composition of claim 9, wherein the total polymer content in the solid phase comprises about 6% to about 8% by weight of polyethylene glycol.

16. The hydrogel composition of claim 9, wherein the hydrogel composition has an osmotic pressure of at least 0.1 MPa.

17. The hydrogel composition of claim 9, wherein the hydrogel composition has a compressive chord modulus of about 450 kPa to about 2,500 kPa.

18. The hydrogel composition of claim 9, wherein the hydrogel composition has a viscosity at 45° C. of about 0.02 kP to about 2.0 kP.

19. The hydrogel composition of claim 9, wherein the hydrogel composition has a viscosity at 37° C. of at least 0.475 kP.

20. The hydrogel composition of claim 9, wherein the composition further includes barium sulfate mixed with the hydrogel composition.

21. The hydrogel composition of claim 1, wherein the hydrogel is a biocompatible hydrogel for intervertebral disc replacement.

22. The hydrogel composition of claim 1, wherein the polyethylene glycol has a molecular weight of about 10,000 Da.

23. The hydrogel composition of claim 9, wherein the polyethylene glycol has a molecular weight of about 10,000 Da.

* * * * *